T. W. HEINEMANN.

SUSPENSORY.

No. 11,369.

Reissued Oct. 3, 1893.

Witnesses:

Clifford N. White

J. L. Devine

Inventor;

Theodore W. Heinemann

By Walter H. Chamberlin

Attorney

UNITED STATES PATENT OFFICE.

THEODORE W. HEINEMANN, OF CHICAGO, ILLINOIS, ASSIGNOR TO THE T. W. HEINEMANN COMPANY, OF SAME PLACE.

SUSPENSORY.

SPECIFICATION forming part of Reissued Letters Patent No. 11,369, dated October 3, 1893.

Original No. 454,168, dated June 16, 1891. Application for reissue filed June 12, 1893. Serial No. 477,402.

*To all whom it may concern:*

Be it known that I, THEODORE W. HEINEMANN, a citizen of the United States, residing at Chicago, Cook county, Illinois, have invented a new and useful Improvement in Suspensories for the Testicles, of which the following is a specification.

My invention relates to the shaping of the testicle-sacks of suspensories, and in describing the same I will refer to the accompanying drawings, in which—

Figure 1:
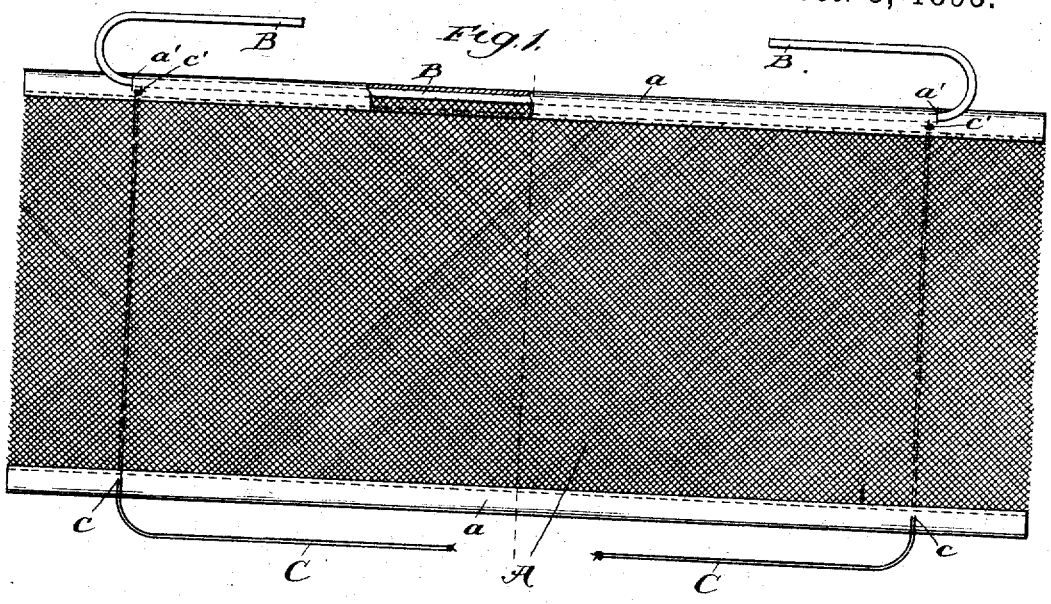
Figure 2:
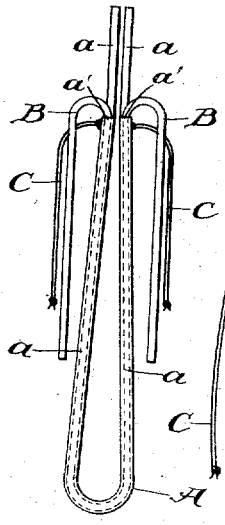
Figure 3:
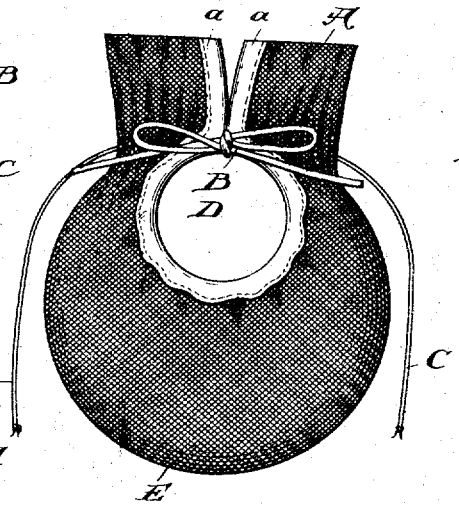
Figure 4:
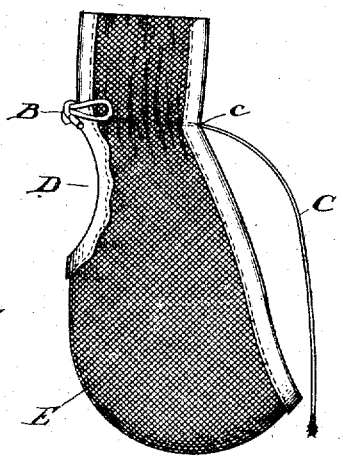

Figure 1 represents a top view of the several parts as they are when at first put together, with a portion of the binding *a* removed so as to show the tape B on the inside. Fig. 2 represents an edge view of the same. Fig. 3 represents a front view of the finished testicle-sack. Fig. 4 represents a side view of the same.

Similar letters refer to similar parts throughout the various views.

I take an oblong piece A of a woven or knitted fabric, which may have double-welt edges, hemmed edges, self-edges, or bound edges. In the drawings this piece A is represented as having bound edges, (marked *a*.) Into one of these bound edges *a*, which I will call the "front" edge (while I will call the other edge *a* the "back" or "posterior" edge), openings are made at each of the two places marked *a'*. Through one of these openings *a'* one end of the tape B is drawn in between the upper and the under fold of the binding *a*, passing along between the two folds until it reaches the other opening *a'*, where it passes out and is cut off in such a way as to leave a length of about two inches of tape hanging out beyond each of the openings *a'*. I then take two strong double threads C. In one end of one of these double threads C, I make a firm large knot. I then take the other end of it and put it through the eye of a needle. By means of this needle I then draw this double thread C first through the binding at *c'* on the left-hand side of Fig. 1, and then in and out through the meshes of the material A at right-angles with the bindings *a* until the needle comes out through the posterior binding *a* at *c*, where I cut off the double thread C in such a manner as to leave a short piece hang out beyond the posterior binding *a* at *c*. I then go through exactly the same operations for the other double thread C, only that this time I do it on the right-hand side in Fig. 1. Next the tape B is drawn as tight as required for the purpose of puckering the front binding *a*, and when this has been puckered sufficiently the ends of the tape B are tied into a bow, as shown in Figs. 3 and 4. In this manner the front binding *a* between the two openings *a'* is made to assume the circular shape D, (shown in Figs. 3 and 4,) which is the most suitable shape for the penis-holes of testicle-sacks. Next the strings C are pulled so as to produce a series of folds nearly parallel to the bindings *a*, and by this operation joined to the forming of the penis-hole D in the manner just described. The lower portion of the piece A is made to assume that ball or pouch shape of testicle-sack which is shown at letter E in Figs. 3 and 4. Similar results can be obtained if the operations hereinbefore described are varied in any of the following ways, viz: if the outhanging ends of the tape B are fastened by sewing or gluing, if the piece A has self-edges and at same time the tape B is made to pass in and out of the meshes of the material of A very close to the front self-edge, or if the front ends of the strings C are fastened by sewing or tying them directly to the material of A, or if elastic cord or flat elastic is substituted for inelastic tape, or if double welts or hemmed edges are used instead of bound edges in the piece A.

I am aware that long before my invention puckering or gathering has been applied to a great variety of purposes and uses in the mechanical arts, and I do not claim to have invented any of these.

I am also aware of the following modes of making testicle-sacks for suspensories in which puckering is one of the results, viz: puckering the posterior binding or sometimes the double welts or the hems of pieces intended for testicle-sacks, forming the penis-hole out of two separate semicircular-shaped edges folded or puckered and afterward bound with elastic braid, and forming testicle-sacks out of pieces into the edges of which rubber threads have been knitted, which has the effect of puckering the pouches; but in all these ways of making testicle-sacks the operations as well as the results obtained are not at all similar to my invention, and I do not claim to have invented any of these; but, Having fully described my invention, what I claim as new, and wish to secure by Letters Patent, is—

1. A suspensory pouch composed of a piece of fabric having a straight front edge, and a string or cord in said edge adapted to draw the edge and pucker it into a circular shape to form the penis-opening, substantially as described.

2. A suspensory pouch composed of a single piece and a tape or cord B, extending along a portion of one of the edges of said piece to draw that portion into a circular shape for a penis-hole and leave a neck to the pouch above the hole, substantially as described.

3. A suspensory pouch composed of a single oblong piece and a tape or cord B, extending along a portion of one of the longer edges of said piece to draw that portion into a complete circle for a penis-hole and leave a neck to the pouch above the hole, substantially as described.

4. A suspensory pouch composed of a single oblong piece and a tape or cord B, extending along a portion of one of the longer edges of said piece to draw that portion into a complete circle to form a penis-hole, and cords C, extending across the rectangular pieces at right angles to the tape or cord B to pucker the neck of the pouch above the penis-hole, substantially as shown and described.

THEODORE W. HEINEMANN.

Witnesses:

W. H. CHAMBERLIN,

J. L. DE VINE.